(12) United States Patent
Piskin et al.

(10) Patent No.: US 10,639,103 B2
(45) Date of Patent: May 5, 2020

(54) OPERATION SCENARIO FLOW AND MECHANICAL MODELING AND ANALYSIS SYSTEM OF CARDIOVASCULAR REPAIR OPERATIONS FOR NEWBORN AND FOETUS

(71) Applicants: Senol Piskin, Istanbul (TR); Kerem Pekkan, Istanbul (TR); Mehmet Berk Yigit, Istanbul (TR)

(72) Inventors: Senol Piskin, Istanbul (TR); Kerem Pekkan, Istanbul (TR); Mehmet Berk Yigit, Istanbul (TR)

( * ) Notice: Subject to any disclaimer, the term of this patent is extended or adjusted under 35 U.S.C. 154(b) by 899 days.

(21) Appl. No.: 15/035,233

(22) PCT Filed: Jul. 11, 2014

(86) PCT No.: PCT/TR2014/000263
§ 371 (c)(1),
(2) Date: May 8, 2016

(87) PCT Pub. No.: WO2015/069202
PCT Pub. Date: May 14, 2015

(65) Prior Publication Data
US 2016/0278866 A1    Sep. 29, 2016

(30) Foreign Application Priority Data

Nov. 8, 2013 (TR) .................................. 2013/12991

(51) Int. Cl.
*A61B 34/10* (2016.01)
*G16H 10/60* (2018.01)
(Continued)

(52) U.S. Cl.
CPC ............ *A61B 34/10* (2016.02); *A61B 5/0022* (2013.01); *A61B 5/021* (2013.01); *A61B 5/0444* (2013.01);
(Continued)

(58) Field of Classification Search
CPC .............. A61B 34/10; A61B 2034/101; A61B 2034/102; A61B 2034/105; A61B 5/0022;
(Continued)

(56) References Cited

U.S. PATENT DOCUMENTS

2007/0014452 A1    1/2007 Suresh
2007/0060785 A1*   3/2007 Freeman ................ A61H 31/00
                                                        600/16
(Continued)

FOREIGN PATENT DOCUMENTS

WO    WO2012021307 A2    2/2012
WO    WO2013071219 A1    5/2013

OTHER PUBLICATIONS

Haifa Hong et al., "Fontan Conversion Templates: Patient-Specific Hemodynamic Performance of the Lateral Tunnel Versus the Intraatrial Conduit With Fenestration" Mar. 9, 2013, Pediatr Cardiol 34:1447-1454 (Year: 2013).*
(Continued)

*Primary Examiner* — Matthew Kremer
*Assistant Examiner* — Avery M Foley
(74) *Attorney, Agent, or Firm* — Bayramoglu Law Offices LLC (57) ABSTRACT

This invention is related to an operation scenario flow, mechanical modeling and analysis system comprising web based, (i) growth (ii) scaling and (iii) quality control aimed, patient based fast prototyping functions, for newborn and fetus cardiovascular repair operations, developed in order to be used for training of doctors and patient specific post surgery performance prediction in hospitals following and prior to, cardiovascular operations within the field of bioengineering in the health sector. Moreover it can be used for both vivo implantation plans of patient specific cardiovascular devices (custom cardiac valve and cardiac support
(Continued)

pumps) and adaptation of said devices to the physiology of the patient.

7 Claims, 5 Drawing Sheets (51) Int. Cl.
*G16H 40/20* (2018.01)
*G16H 50/50* (2018.01)
*G16H 10/40* (2018.01)
*A61B 5/00* (2006.01)
*A61B 5/021* (2006.01)
*A61B 5/0444* (2006.01)
*A61B 90/00* (2016.01)

(52) U.S. Cl.
CPC ............ *G16H 10/40* (2018.01); *G16H 10/60* (2018.01); *G16H 40/20* (2018.01); *G16H 50/50* (2018.01); *A61B 2034/105* (2016.02); *A61B 2090/374* (2016.02); *A61B 2090/378* (2016.02); *A61B 2090/3762* (2016.02); *A61B 2503/02* (2013.01); *A61B 2503/045* (2013.01)

(58) Field of Classification Search
CPC . A61B 5/021; A61B 5/0444; A61B 2090/374; A61B 2090/3762; A61B 2090/378; A61B 2503/02; A61B 2503/045; G16H 40/20; G16H 40/60; G16H 50/50; G16H 10/40; G16H 10/60

See application file for complete search history.

(56) References Cited

U.S. PATENT DOCUMENTS

| | | | | |
|---|---|---|---|---|
| 2011/0274566 A1* | 11/2011 | Amirouche | ....... | A61M 5/14224 417/322 |
| 2012/0053918 A1* | 3/2012 | Taylor | ................ | A61B 5/02007 703/9 |
| 2014/0200867 A1* | 7/2014 | Lavi | ..................... | G06F 19/321 703/2 |

OTHER PUBLICATIONS

Onur Dur et al "Pulsatile venous waveform quality affects the conduit performance in functional and "failing" Foutain circulations", Cardiology in the Young, vol. 22, No. 03, Oct. 19, 2011, pp. 251-262.

Andres Ceballos "A Multiscale Model of the Neonatal Circulatory System Following Hybrid Norwood Palliation", Aug. 1, 2011.

* cited by examiner

OPERATION SCENARIO FLOW AND MECHANICAL MODELING AND ANALYSIS SYSTEM OF CARDIOVASCULAR REPAIR OPERATIONS FOR NEWBORN AND FOETUS

TECHNICAL FIELD OF THE INVENTION

This invention is related to an operation scenario flow, mechanical modeling and analysis system comprising web based, (i) growth (ii) scaling and (iii) quality control aimed, patient based fast prototyping functions, for newborn and fetus cardiovascular repair operations, developed in order to be used for training of doctors and patient specific post surgery performance prediction in hospitals following and prior to, cardiovascular operations within the field of bio-engineering in the health sector. Moreover it can be used for both vivo implantation plans of patient specific cardiovascular devices (custom cardiac valve and cardiac support pumps) and adaptation of said devices to the physiology of the patient.

BACKGROUND

The doctor faces several operation scenarios in the treatment of cardiovascular diseases via operation, during which blood circulation performance carries great importance. The doctor decides upon one of these scenarios by taking into consideration the ideas and opinions of other doctors and his own experiences. Moreover the doctor examines prior cases and their results. The doctor gives a final decision by taking into consideration all these facts. Estimating the changes that will occur in the cardiovascular system following an operation, as mentioned above, according to the known state of the art, could be misleading in many cases and may necessitate far too much experience. Moreover many cases and their results may be overlooked and they may not be examined in sufficient detail. The decision processes during fetus and newborn operations are even more difficult, because the systems of these patients are more complex in comparison to adults and they are also more susceptible to change. Moreover the patient's cardiovascular system keeps growing together with their body and their tissue characteristics continue to change. The decisions must be given specific to the patient and the artery, vein and artificial material's vein sizes must be taken into consideration. This growth and change of structure mentioned above is three dimensional and it is quite difficult to estimate. In addition to these, the heights of the patients and their circulatory networks are different from each other. It is not possible to normalize hemodynamic performance parameters. There is no system which takes these effects into consideration. Scaling is especially important during the fetal stage where the cardiovascular system continues to develop and the present invention is also advantageous in planning fetal cardiac interventions.

Taylor et al. (wo 2012/021307) proposed a patient specific cardiovascular treatment planning. In their system they acquire patient specific medical image (i.e. CT), physiologic data (blood pressure, heart rate and etc.) and cardiac perfusion data. They create the 3D model of the patient's heart and vessels. They allow the user to modify the created model. They run the computational fluid dynamics simulation on the modified model and show the results of the modification. They proposed to deliver this service via the web site.

Suresh et al (US 2007/014452)proposed a segmentation algorithm to process the medical image of the patient and create a 3D model of heart. The system offers treatments to the user. The user selects the treatment he or she desires. The clinical outcome of the selected treatment is given to the user as end result. Sharma et al. (WO 2013/071219) proposed a more specific system for multi-scale anatomical and functional modeling of coronary circulation. Dur et al. (Cardiology in the young, vol. 22, no. 3) and Ceballos et al. (a multiscale model of neonatal circulatory system following hybrid norwood palliation) did studies on the congenital heart disease surgeries. Dur et al. proposed a novel performance parameter to quantify the energy efficiency of Fontan venous waveforms in pulsatile settings. Ceballos et al. developed a multi-scale model to to understand the local hemodynamics after Hybrid Norwood procedure.

SUMMARY OF THE INVENTION

A system which can carry out the following especially in fetus and newborn cardiovascular surgeries has been aimed, when improving operation scenario flow, mechanical modeling and an analysis system to be used during newborn and fetus cardiovascular repair operations developed by means of this invention, To plan the operation to be carried out on the patient and the techniques to be used, prior to the operation in a virtual environment.

To be able the present to the evaluation of the user, the estimations taken regarding the results to be anticipated from the operation, via quantitative models produced, using engineering tools having industrial standards, visually and statistically, To create a model together with the cardiovascular structure of the blood flow, using data belonging to the patient and the plans that the doctor shall carry out, To estimate the changes that shall occur in tissue characteristics and how the cardiovascular system will take form and also the natural development of the patient, To be able to present the operation results not only transiently but also taking into consideration the growth that shall occur in time, To be able to integrate heart function calculations (patient based, as threshold value) and peripheral circulation (microcirculation) to the operation results.

It is aimed for this operation scenario flow, mechanical modeling and analysis system to that has been developed according to the present invention for newborn and fetus cardiovascular repair operations to be used in cases where numerical models and intuitive estimations are not sufficient and as an aid to doctors during the decision stages regarding surgical operations by the presentation of statistical and visual information. As a result, the percentage of error in relation to the operations that are to be carried out on complex structures for which the doctor cannot carry out estimation by only depending on his/her own experience can be significantly decreased. Consequently, the estimated scenarios typical to the operations will be able to be carried out independent from the experiences of the surgeons and as a result the number of specialists that will be able to perform said surgical operations will be increased.

The success rate of operations where the operation scenario flow, mechanical modeling and analysis system is applied for newborn and fetus cardiovascular repair operations developed according to the invention shall be increased by means of this model and together with this, the fatality risks that could occur during the operations of fetus and newborn babies will also be decreased. In the known state of the art, in several cases the fetus and new born babies may need multiple operations. One of the reasons for multiple operations to be carried out is because it is difficult to correctly estimate the growth process and the mechanical characteristics of the cardiovascular system prior to an operation and following an operation. This situation increases the necessary number of operations and the occurrence of unwanted situations. The modeling techniques of the system developed according to this invention will also help decrease the number of operations.

BRIEF DESCRIPTION OF THE DRAWINGS

The drawings prepared in order to be able to better explain the operation scenario flow, mechanical modeling and analysis system for newborn and fetus cardiovascular operations developed according to the present invention have been attached to this description. The description of the drawings has been mentioned below.

FIG. 1—Shows the hardware structure of the system developed according to this invention. The high speed prototype device with which the suggested patient based, surgical configuration is checked has not been shown here, FIG. 2—Shows the electrical circuit (network) that is used in the circulation model, the compartmentalizing techniques used in the scaling system and the circuit members.

The parts in the figures that have been prepared in order to better explain the operation scenario flow, mechanical modeling and analysis system to be used in newborn and fetus cardiovascular repair operations developed according to the present invention have each been numbered. The references of the numbered have been listed below.

1: User (PC)
2: Server
3: Host computer
4: Web cloud
5: Task entry and result notification
A: Circuit network of the circulation segment
B: Compartments
C: Resistances
i and j: Node points
Sis: Systemic
Pul: Pulmonary,
Art: Artery,
Ven: Vein,
SVR: Systemic vascular resistance
PVR: Pulmonary vascular resistance
V: Ventricle (Ventricle-Heart)

DESCRIPTION OF THE INVENTION

Figure 1:
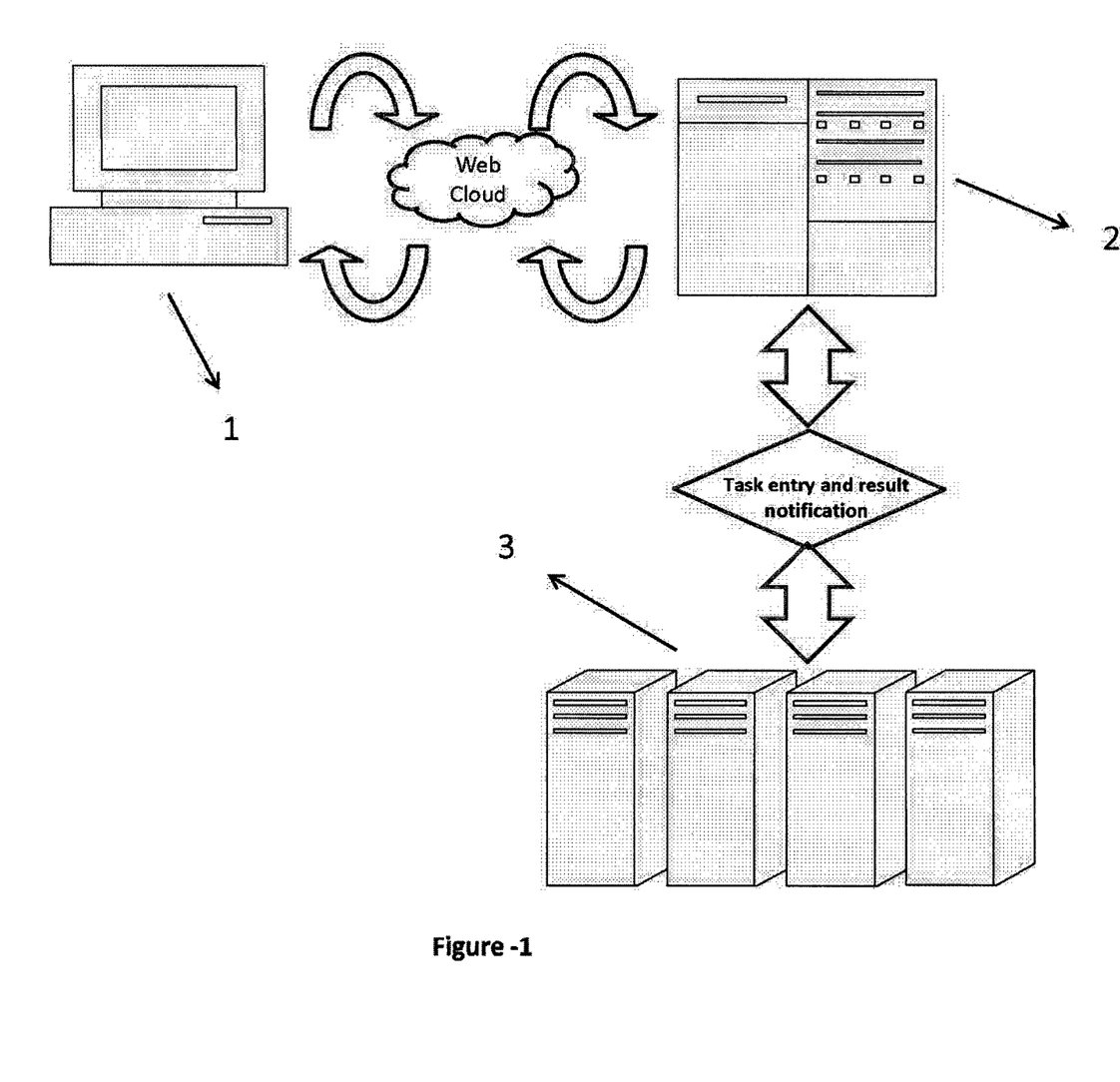

The operation scenario flow, mechanical modeling and analysis system for newborn and fetus cardiovascular operations developed by means of the present invention basically comprises the following:
A user computer—PC (1),
Server (2),
Host computer (3),
Web cloud (4),
Task entry and result notification (5), and
Models/Software The user computer—PC (1) is a PC having standard characteristics that can be connected to the internet, developed to be used for standard end users. It comprises input/output units for keyboards and a mouse. It is presumed that the users already own such a computer. The PC should be installed with commonly used operating systems and again with commonly used internet browsers. The user uses this computer to send the information such as MRI/CT, echo, ECG data of the patient via the internet to the server. The user forms the operation scenario in the interface of the internet page, by using the input/output tools such as the keyboard and the mouse of the computer. During this stage, the user can cut the veins from any section or at any angles he/she prefers, the user can by-pass any of the veins or the ventricle; can connect any of the veins from any point he/she desires; and make any other necessary changes for the operation. This new operation scenario geometry that has been established by the user is submitted to the server computer via the internet.

The server computer (2) is a more powerful server type computer in comparison to a standard PC. The server must be able to respond to the prompts that can be received from tens or hundreds of user PC's (1) at the same time. The server processes the prompts received from user PC's (1) through the internet and establishes the operation estimation model. This model uses the real geometries, echo, ECG data, age, weight information belonging to the patient. The model that has been formed is sent to the host computer in order for a simulation to be carried out. The results of the simulated model are received from the host computer and are converted into the data that the user doctor requests. This data can be the flow rate sent to the organs, the blood that the heart can pump, and the energy required by the functioning of the heart. The data obtained is sent via the internet to the user PC (1).

Moreover the cardiovascular geometry of a patient is formed automatically, within the server (2) using the patient screening data such as CT/MRI which have been received from the user PC (1). The geometry that has been formed is sent back to the user PC (1) via the internet. The user can see this geometry on his/her screen by means of the internet interface and can examine the cardiovascular system of his/her patient, from the inside and the outside and from various angles. The user forms the operation scenario using this geometry and sends the scenario information to the server.

The server computer (2) shall have a database which can store all models and results. The users should then be able to see the previously entered patient data, geometries that have been formed, the scenarios, and the results that have been obtained within the framework of security and authorization protocols.

The host computer (3), is a more powerful computer system which can carry simulation of multiple models at the same time, wherein more than one computer with multi processors can be connected to each other via network connection. The model information received from the server is converted into real calculation models and is solved. This analysis is carried out by means of, previously installed various software. These software, are specialized software in carrying out computational structural analysis (HYA), computational fluid mechanics (HAM), structural fluid interaction, solving differential equation with ordinary derivatives and partial derivative differential equations. The software to be used to solve the models is defined in advance on this host computer.

The models and software herein, have been designed to have the following characteristics: determining what kind of limit conditions should be established for methods such as HAM, HYA for values like echo, blood pressure belonging to the patient; scaling with data such as weight, volume of the patient; new structure of the operation scenario that will be formed after the patient grows; determining the perfusion, flow rate value of the patient following operation; determining how the cardiovascular system (using MRI/CT data dependent on time) of the patient will change due to pressure or by means of the MRI/CT data of the material characteristics of the cardiovascular system of the patient and using these material characteristics in the HYA software; determining the blood resistance values again using MRI/CT data and using them in the HAM, HYM and AYE software.

Figure 2:
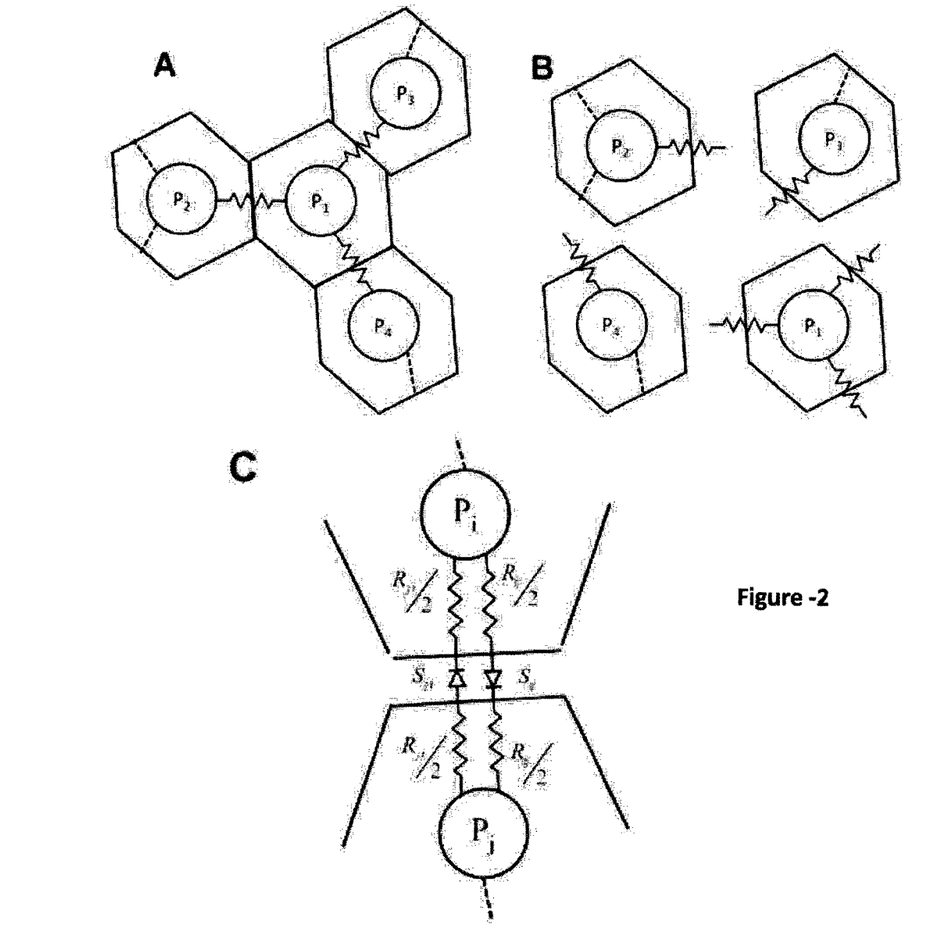

In FIG. 2, the electrical circuit (network) used in the circulatory model, compartmentalizing technique and circuit means have been shown. The circulation model of the patient is established by using the anatomical characteristics of the disease and the flow and pressure measurements taken from the cardiovascular system and parameters related to the model are calculated. In the simplest pressure flow model within this method, electrical circuit analogy is used (1B modeling). There are two types of circuit means in the nodes, which are the capacitance (C) and resistances at the sides. The pressure values (P) on the model have been defined such that they can be measured on the nodes. The circuit network (A) of the model can be classified into sections (B) having a node point (i) in each, and carrying sides (l,j) that connect this node point to adjacent node points. (C) In the method used, the side that connects any one of the node pairs (i,j), comprises diodes ($S_{ij}, S_{ji}$) that allow single direction flow and two resistances ($R_{ij}, R_{ji}$) (as different values can be taken depending on the flow direction of the resistor, the necessary indices have been used to represent the resistor at the flow direction: ij shows the flow from i to j and ji shows the flow from j to i). During compartmentalizing the resistances are distributed equally between two adjacent sections. The aim of the compartmentalizing method, is to be able to evaluate/examine the circulatory system and model modularly and to be able to apply the scaling/growth methods used on the basis of compartments. The parameters for each compartment during scaling, have been made to be "non dimensional" using Buckingham Pi Theorem. The parameters that have been developed within the scope of this invention; is $$\omega RC, \frac{C_{min}}{C_{max}}, \frac{P_i}{P_o}, \frac{Q}{\omega CP_0}, \frac{E}{\omega CP_0^2}$$

Wherein, $\omega$: is the pulse frequency, R: is resistance, C: capacitance, min/max: minimum maximum (related to the ventricles); $P_i$: the blood pressure measurement in a section; $P_0$: blood circulation pressure, Q: flow, and E: is energy loss. In the method improved by the operation scenario flow and mechanical modeling and analysis system for newborn and fetus cardiovascular repair operations developed according to the present invention, "normal" and "sick/abnormal" value ranges have been determined by taking into consideration the age/weight/clinical characteristics of the patient, type/etc of the diseases, for the non dimensional parameters. These ranges are determined from databases that can additionally be formed from academic and clinical literature.

Figure 3:
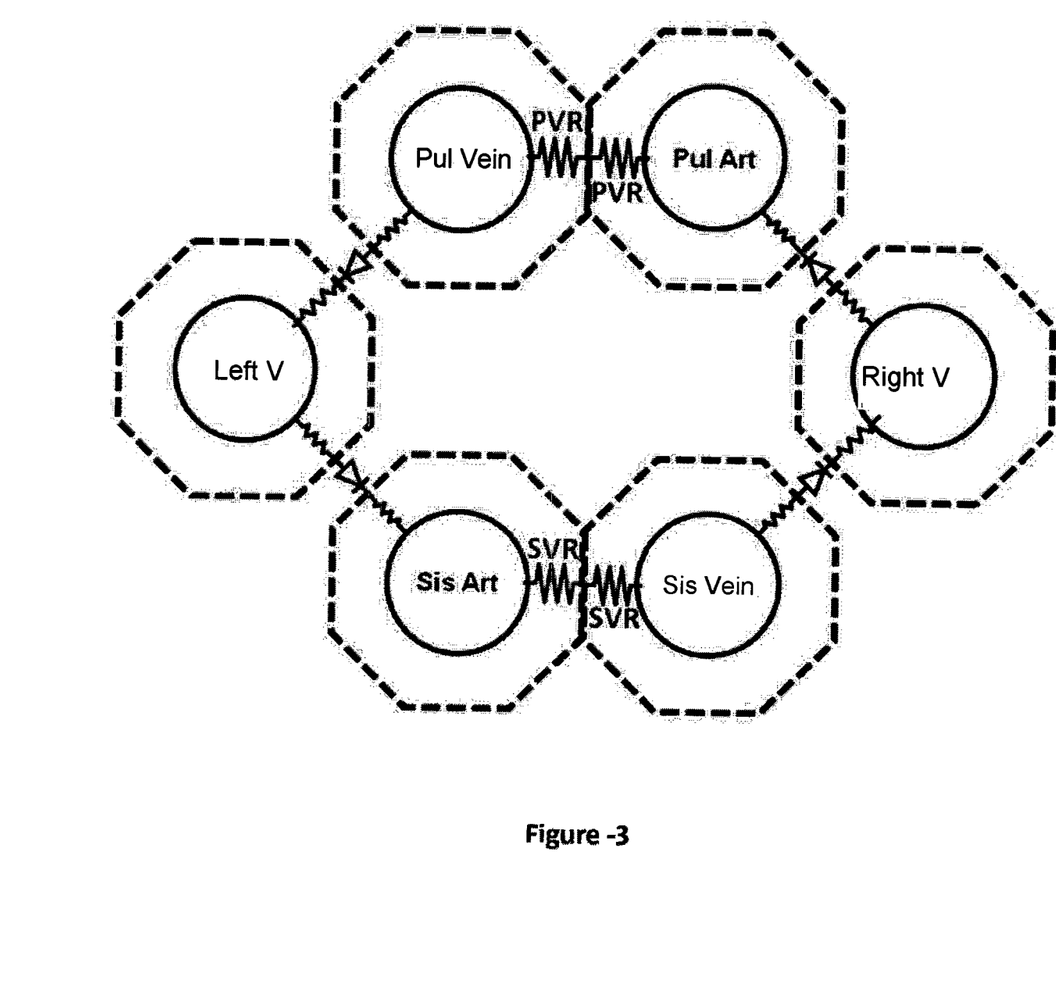
FIG. 3—Shows an illustrative circuit model obtained by the compartmentalizing method using the circulation anatomy of the patient.

In FIG. 3, an illustrative circuit model is shown which has been obtained by means of a compartmentalizing method based on the circulation anatomy of the patient. According to the anatomic information of the patient, the circulation model (circuit) of the patient is formed. This model is formed basically only by using the electrical circuit means explained in the previous stage. The circulation anatomy of a healthy person can be defined by an electrical circuit comprising six sections (sections illustrated with striped hexagons). Sections can be added/omitted/modified by adding circuit means/changed with higher order models (higher order, for example 2-B or 3-B) in order to increase the details at the section that is to be examined and/or in accordance with the anatomical differences of a patient. The flow rate, pressure or material characteristics of the patient can be used in order to calculate the parameters of the model. In order to reach this aim, HAM calculations, classical hydrodynamic and electrical equations (Hagen-Poiseuille, etc.) in connection with flow-pressure and geometry can be used. If the sections used in the model are solved with HAM techniques in 3D, more realistic results can be obtained. For this reason these calculations must be preferred as far as possible. However sufficient amount of data may not be valid in all cases and in order to obtain a quick result the 1D modeling methods mentioned above are used.

Figure 4:
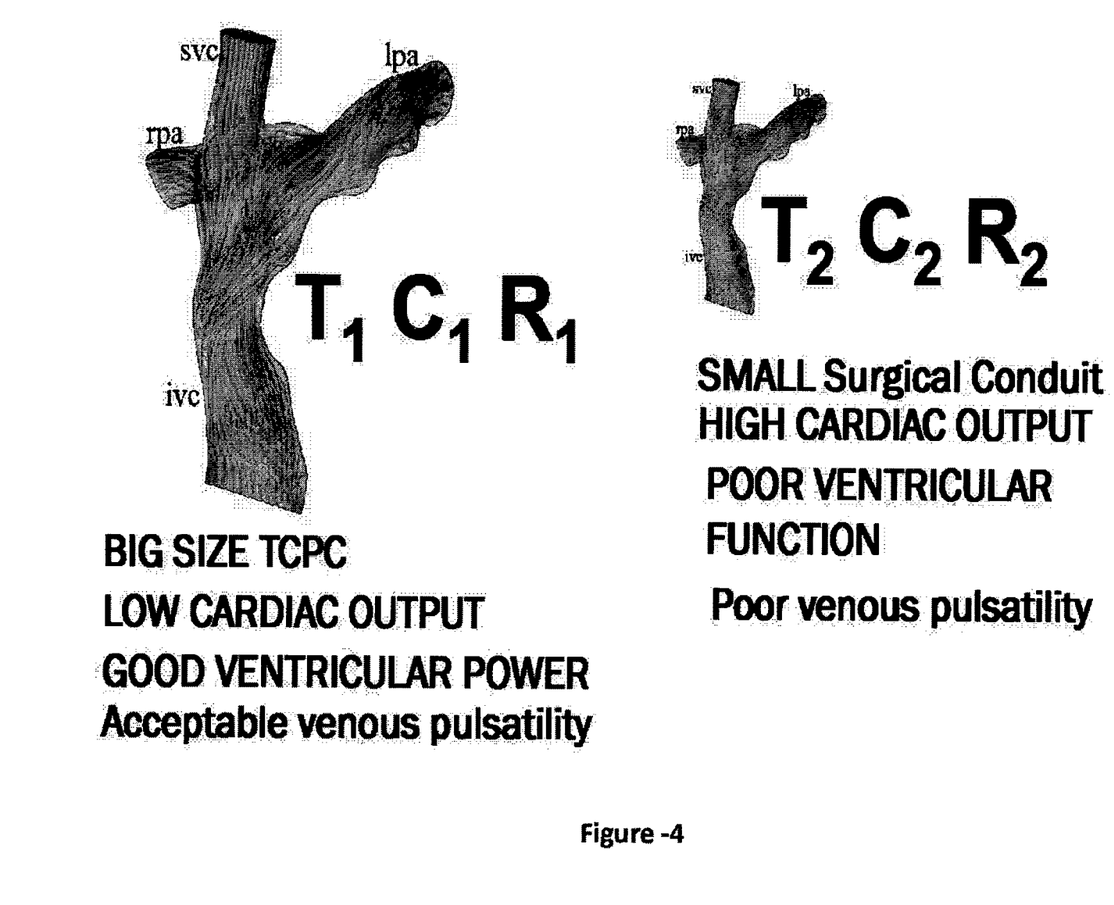
FIG. 4—Shows the basic parameters that the invention can scale and the illustrative surgical conduit that is simulated (T: time, C: Compliance, R: Flow resistance)

FIG. 4, shows the illustrative surgical conduits of the simulation and the basic performance parameters that the invention can scale (T: Time, C: Compliance, R: Flow resistance).

Figure 5:
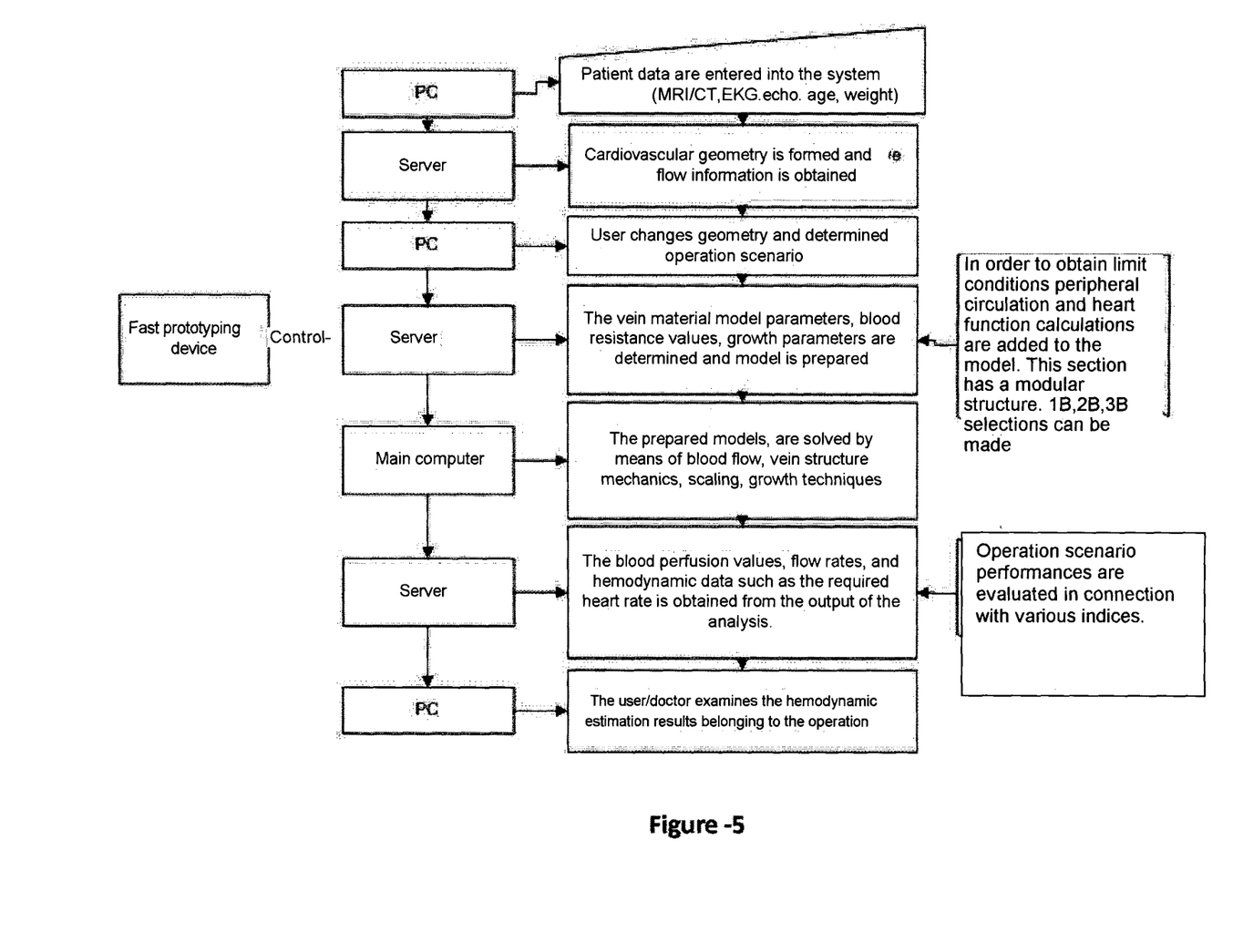
FIG. 5—Shows the flow diagram developed according to the invention

FIG. 5, shows the flow diagram of the system. A model of the cardiovascular system, is created mechanically and solved; by means of the operation scenario flow, mechanical modeling and analysis system for newborn and fetus cardiovascular repair operations developed according to the present invention.

For a model to be created;
First of all various data such as CT/MRI, echo, ultrasound of the patient is uploaded to the system via the internet. The rate and pressure data depending on the time received from the circulation system together with the cardiovascular system geometry are automatically obtained by means of a server.
In the next stage, the doctor who will be performing the operation decides on the operation scenario via the internet using tools such as the mouse etc. of the PC. The simulation of this operation scenario is carried out using the model that has been created. During the simulation, computational fluid mechanics, computational structural mechanics techniques are used. The model parameters are obtained automatically using the clinical data that the doctor has sent within the framework of the protocols prepared by the model parameters.

The model formed according to the operation scenario flow, mechanical modeling and analysis system for newborn and fetus cardiovascular repair operations developed according to the present invention comprises many non linear characteristics of the cardiovascular system in order to create a realistic simulation. It has been taken into account without having flow characteristics according to Kan Newtonian and the cardiovascular tissue is modeled by taking into account micro and macro mechanical characteristics.

Moreover the geometric changes of the patient dependent on time and the tissue parameters of the patient are obtained and used in modeling. The model of the operation scenario flow, mechanical modeling and analysis system for newborn and fetus cardiovascular repair operations that has been developed according to this invention, is customized especially for the fetus and newborns and it takes into consideration their growth and tissue characterization changes in time. Various scaling methods used in order to reach this aim, ensure that the difficulties faced when evaluating the circulation parameters depending on the size of the body and the cardiovascular performance analysis, are overcome.

Local and general evaluations are carried out by means of said scaling methods. Following operation, the growth of the cardiovascular system foreseen by the model is monitored and the healing process of the patient can be evaluated and new estimations can be made by updating the model according to the situation of the patient.

While these procedures are being carried out, in order to determine the hemodynamic performance of the surgical operations, many hemodynamic performance indices such as, the cavo pulmonary pressure gradient (CPPG), loss of strength, hepatic flow distribution etc. shall be used. These values shall be calculated along the respiration cycles and their average is calculated. Other parameters in addition to these parameters can also be determined. The differences between the average vena cava pressure and the bilateral pulmonary artery (PA) pressure are used in order to calculate CPPG.

The total caval flow pulsatile index (TCPI) is obtained as a percentage of the ratio of the flow rate of the total vein calculated by taking the average in time of the total fluctuating flow component of the total vein. The Stagnant flow index (SFI) is used to determine the stagnant sections inside the cardiovascular system and their sizes quantitatively. When this value is being calculated, the values of the blood resistance time of the cardiovascular circuits are used.

The modeling results in the operation scenario flow, mechanical modeling and analysis system for newborn and fetus cardiovascular repair operations developed according to this invention can be observed via the web by the doctor. All of the data are stored within secure cloud storage systems such that they can be accessed by the doctors whenever they wish. Some patient data, operation scenarios, results, growth information, success statistics can be shared via the system developed according to this invention when desired.

The procedures of the operation scenario flow, mechanical modeling and analysis system for newborn and fetus cardiovascular repair operations developed according to this invention are performed by carrying out the following steps:

1) The user connects to the web page of the system via a standard web browser, using his/her PC (1) and connects by entering his/her user name and password
2) The user creates a new patient log. (In this step the identification information of the patient is not entered due to security reasons. The system assigns a suitable patient registration number for the patient. The user/doctor records this patient number to his patient file at the hospital).
3) The user uploads data such as the MRI/CT, echo, ECG, blood pressure results, and weight of the patient to the system.
4) The web system transfers such data to the server (2) via the internet,
5) The server automatically obtains the three dimensional (3D) geometry of the cardiovascular system by means of the previously loaded software,
6) The server sends the 3D geometrical data it has obtained, to the user through the internet and the cardiovascular system is formed if desired by the user by means of the fast prototyping device. (If necessary artificial/organic tissue can be used during this step).
7) The user, uses the web interface in order to examine the geometry from various angles and to carry out changes to the geometry if he/she wishes,
8) The operation scenario that is being planned to be carried out is formed by the user using the geometry. (When the user is carrying this out; he/she can cut the veins from any of the points and shorten them; can add veins and lengthen them: can constrict or enlarge the veins; can by-pass any vein section or ventricle; can connect any of the veins to veins of any thicknesses, from any angle or section he/she wishes)
9) The user notifies via the web that the scenario has been created,
10) The user can create if he/she desires, different scenarios for the same patient,
11) The scenario information that has been created is transmitted to the server through the web.
12) The material mode parameters of the veins from the data belonging to the patient, the blood resistance values, scaling and growth parameters are available automatically in the server and as it can be seen in FIG. 2 and FIG. 3, the electrical circuit analogy is used. The circulation model and the parameters related to the model are calculated, based on the anatomical characteristics of the disease and the flow and pressure measurements taken from the cardiovascular system. Electrical circuit analogy is used in the most simple pressure flow model in this method (1D modeling). The parameters belonging to each section during scaling are "non dimensionalized" using Buckingham Pi Theorem. During this stage the parameters $$\omega RC, \frac{C_{min}}{C_{max}}, \frac{P_i}{P_o}, \frac{Q}{\omega CP_0}, \frac{E}{\omega CP_0^2}$$

are used. Wherein $\omega$: is the pulse frequency, R: is resistance, C: capacitance, min/max: minimum maximum (related to the ventricles); $P_i$: the blood pressure measurement in a section: $P_0$: blood circulation pressure, Q: flow, and E: is energy loss. In the method improved by the operation scenario flow and mechanical modeling and analysis system for newborn and fetus cardiovascular repair operations developed according to the present invention, "normal" and "sick/abnormal" value ranges have been determined by taking into consideration the age/weight/clinical characteristics of the patient, type/etc of the diseases, for the non dimensional parameters. These ranges are determined from databases that can additionally be formed from academic and clinical literature.

13) Compartmentalizing method is applied (It is possible to evaluate/examine the cardiovascular system and models modularly and to apply the scaling/growth methods used based on sections. This way, the desired sections can be added to the model as 1D, 2D or 3D images. 1D modeling gives faster results, whereas 3D modeling can provide more realistic results. These preferences, dependent on the data/time have been left to the doctor/user's choice).
14) The parameters, data, geometry, scenarios, model information obtained, are sent to the host computer (3) via the internet.

15) The simulation of the model is performed by means of the software installed on the host computer (3) and the values following operation are obtained haemodynamically.
16) The data obtained are again sent to the server (2) over the internet.
17) The server (2) receives the simulation results, processes them, and produces the blood perfusion flow rate values belonging to the patient using these results. (During this stage the amount of energy that is required for the heart to operate under various scenarios are determined. Moreover various indexes are used in order to calculate the operation scenario performance: Total caval flow pulsatile index (TCPI), is obtained by giving the rate to the total vein flow whose average rate has been taken from the total vein flow fluctuating component in time. Stagnant flow index (SFI) is used to determine the sections and sizes that are stagnant inside the cardiovascular system. This index is obtained by dividing the stagnant blood volume inside the index conduit to the total volume and then multiplying it by a hundred. When the stagnant blood volume is being calculated, the blood resistance times (RT) of the cardiovascular circuits are used. If the RT is over certain values, this volume is defined as the stagnant volume).
18) The data produced are sent via the internet to the user PC (1).
19) The user receives the values
20) The user creates new scenarios if he/she desires
21) The user logs out of the system.

The operation scenario flow and mechanical modeling and analysis system, for newborn and fetus cardiovascular repair operations developed according to the present invention is characterized in that it provides the following:

Operation scenario planning for the fetus's
Operation scenario planning for the newborn
An operation scenario plan comprising the growth following operation
Modeling of the fetus and newborn growth together with scaling
Planning the operation scenarios of the fetus and the newborn using the scaling technique and by taking into consideration the growth and the change in time of the tissue characteristics and estimating the change of the operation results together with age
Modeling the growth of the fetus and the newborn together with the scaling method that is compatible to all circulation systems.

The operation scenario flow and mechanical modeling and analysis system, for newborn and fetus cardiovascular repair operations developed according to the present invention can be used to test the bio inspired designs faster and to apply them to life. The CT/MRI data of various other living beings can also be used instead of using patient data. The changes that may be desired to be carried out on the geometries that shall be obtained can be carried out using the system improved with this invention.

The invention claimed is:

1. A patient based operation scenario flow method, wherein patient data are entered into a system and cardiovascular geometry is formed and flow information is obtained for newborn and fetus cardiovascular operations comprising the steps of:
a) changing the cardiovascular geometry and determining an operation scenario using patient growth;
b) applying compartmentalization to distribute a plurality of resistances equally between two adjacent sections of a cardiovascular system to scale a cardiovascular performance of the patient to evaluate and/or examine the circulatory system of the patient and model modularly and to apply scaling and/or growth methods on each compartment that will enable post-surgery performance prediction and comparison by using previously entered patient data, formed cardiovascular geometries, a plurality of scenarios, and a plurality of results;
c) obtaining scaling and growth data for body size, mechanical characteristics of a cardiovascular system and blood flow that the patient's heart can pump;
d) obtaining limit conditions by determining and preparing models for vein, artery or artificial vein model parameters, blood resistance values and growth parameters using peripheral circulation and heart function calculations;
e) solving the prepared models by using the blood flow, vein structure mechanics, scaling parameters and the growth parameters to estimate changes in the patient's tissue characteristics, a future form of the patient's cardiovascular system, and a natural development of the patient;
f) determining an amount of energy required by the heart to operate;
g) examining hemodynamic estimation results of the operation scenario; wherein, a hemodynamic performance of the operation is determined by a plurality of hemodynamic performance indices comprising a cavo pulmonary pressure gradient (CPPG), loss of strength, and a hepatic flow distribution calculated along a plurality of respiration cycles; wherein, the CPPG is calculated by using differences between an average vena cava pressure and a bilateral pulmonary artery (PA) pressure.

2. The method according to claim 1 where the patient data is obtained by determining limit conditions for values MRI/CT, echo, ECG, blood pressure results, and weight of the patient; scaling data comprising the patient's weight, body size, and mechanical characteristics of the cardiovascular system; determining a perfusion and a blood flow rate value of the patient following operation; determining how the cardiovascular system of the patient will change due to pressure; and determining blood resistance values.

3. The method according to claim 1 where the compartmentalizing is applied according to the steps of:
forming a circulation model of the patient by using an electrical circuit and applying the compartmentalization;
calculating the parameters of the model with computational fluid mechanics, computational structural analysis, structural fluid interaction calculations, growth mechanics, classical hydrodynamic or electrical equations in connection with flow-pressure and the cardiovascular geometry.

4. The method according to claim 1, further comprising using an electrical circuit analogy to obtain and make automatically available in a server: the vein, artery or artificial vein material model parameters, the blood resistance values, compliance values, the scaling and growth parameters; wherein the circulatory model of the patient is created based on anatomical features of a disease, a pressure and flow rate measurements taken from the cardiovascular system; and a plurality of parameters related to the model are calculated.

5. The method according to claim 1, further comprising using the Buckingham Pi Theorem to non-dimensionalize the scaling parameters, the growth parameters and the vein, artery or artificial vein material model parameters for each section at the stage of scaling for obtaining the scaling parameters, the growth parameters and the vein, artery or artificial vein material model parameters, the blood resistance values, the growth parameters and flow parameters which are represented as:

$$\omega RC, \frac{C_{min}}{C_{max}}, \frac{P_i}{P_o}, \frac{Q}{\omega CP_0}, \frac{E}{\omega CP_0^2}$$

wherein, $\omega$ is a pulse frequency, R is resistance, C is capacitance; $P_i$ is blood pressure measurement in a section, $P_0$, is blood circulation pressure, Q is flow, and E is energy loss.

6. The method according to claim 1, further comprising obtaining a total caval flow pulsatile index (TCPI), by giving a rate of a total vein flow whose average rate has been taken from a total vein flow fluctuating component in time; and calculating an operation scenario performance using the TCPI.

7. The method according to claim 1, further comprising obtaining a stagnant flow index (SFI) by dividing a stagnant blood volume inside an index conduit by a total volume and then multiplying by a hundred, in order to quantitatively determine locations and sizes of stagnant sections inside the cardiovascular system, in order to calculate an operation scenario performance.

\* \* \* \* \*